United States Patent [19]
Tanaka

[11] Patent Number: 5,928,175
[45] Date of Patent: Jul. 27, 1999

[54] MEDICAL CORSET WHICH COMPRESSES SACROILIAC REGION AND/OR HIP JOINT REGION TO LIGHTEN LAME HIP

[75] Inventor: Nobutaka Tanaka, Daito, Japan

[73] Assignee: Tanaka Planning Corporation, Osaka-fu, Japan

[21] Appl. No.: 08/747,661

[22] Filed: Nov. 13, 1996

[30] Foreign Application Priority Data

Nov. 17, 1995 [JP] Japan ..................................... 7-300005

[51] Int. Cl.⁶ .................................................. A61F 13/00
[52] U.S. Cl. .............................. 602/75; 450/146; 602/23; 602/62
[58] Field of Search .................................. 602/19, 24, 53, 602/65, 75, 23, 60, 61, 63, 79; 623/901; 2/45; 128/845, 846, 101.1, 106.1; 450/154, 146; D24/2, 49, 64

[56] References Cited

U.S. PATENT DOCUMENTS 3,783,879   1/1974   Stalder .
4,576,154   3/1986   Hyman et al. .
4,709,692   12/1987  Kirschenberg et al. .
4,926,845   5/1990   Harris .
5,161,257   11/1992  Arsendorf et al. ............................ 2/455
5,423,852   6/1995   Daneshvar ................................ 602/53
5,425,702   6/1995   Carn et al. .

FOREIGN PATENT DOCUMENTS

0636325 A2   2/1995   European Pat. Off. .
0636325 A3   11/1995  European Pat. Off. .

*Primary Examiner*—Richard J. Apley
*Assistant Examiner*—Kim M. Lee
*Attorney, Agent, or Firm*—Rabin & Champagne, P.C

[57] ABSTRACT

A medical corset according to the present invention includes a hip band portion composed of an elastic material for covering both the sacroiliac region and the hip joint region and a pair of femoral region holding portions coupled below the buttock portion of this hip band portion to be fixed on the thighs. When this corset is put on a body, the sacroiliac region and the hip joint region are compressed and protected by the hip band portion and a lame hip due to a trouble of these joints is lightened.

11 Claims, 7 Drawing Sheets

MEDICAL CORSET WHICH COMPRESSES SACROILIAC REGION AND/OR HIP JOINT REGION TO LIGHTEN LAME HIP

BACKGROUND OF THE INVENTION

1. Field of the Invention

The present invention relates to corsets, and particularly to a medical corset for lightening a lame hip.

2. Description of the Background Art

A lame hip is usually caused when the femoral nerves running near the hip joints or the sciatic nerves running near the sacroiliacs are stimulated.

As shown in FIG. 7, the sciatic nerves $21a$, $21b$ run near the sacroiliacs $13a$, $13b$ serving as joints between the sacrum 12 and the iliums $11a$, $11b$ of the hip bones. The femoral nerves $22a$, $22b$ run near the hip joints $16a$, $16b$ serving as joints between the thighbones $17a$, $17b$ and the iliums $11a$, $11b$.

The sacroiliacs $13a$, $13b$ are plane joints which do not move much. If a problem occurs in this region and the jointing force between any of the iliums $11a$, $11b$ and the sacrum 12 decreases, however, the two will move in an unusual direction relative to each other. When the ilium $11a$ and the sacrum $12a$ move in an unusual direction relative to each other, for example, the sciatic nerve $21a$ running in its vicinity is stimulated to cause a lame hip.

If a disease occurs in the hip joint $16a$ and the jointing force between the ilium $11a$ and the thighbone $17a$ is decreased, for example, then the thighbone $17a$ will move in an unusual direction with respect to the ilium $11a$. Then, the thighbone $17a$ moving in the unusual direction stimulates the femoral nerve $22a$ running near the hip joint $16a$ to cause a lame hip.

Conventional medical corsets include one formed into a simple band-like shape 9, which is wound around the body to surround the lumbar vertebrae $18a$, $18b$ which extend above the sacrum 12 as shown in the figure to surely keep the lumbar region quiet. Accordingly, this produces some effect to reduce a lame hip due to a problem of the lumbars $18a$, $18b$ and the intervertebral disks interposed therebetween.

However, the conventional medical corset 9 described above is intended to keep the region of the lumbars $18a$, $18b$ quiet, which can not effectively prevent a lame hip due to a trouble of the sacroiliacs $13a$, $13b$ or the hip joints $16a$, $16b$.

SUMMARY OF THE INVENTION

An object of the present invention is to protect the sacroiliac region to effectively prevent a lame hip due to problems in this region.

Another object of the present invention is to protect the hip joint region to more effectively prevent a lame hip.

In order to achieve the objects above, a medical corset according to an aspect of the present invention includes a hip band portion composed of an elastic material for covering both the sacroiliac region and the hip joint region and a pair of femoral region holding means coupled to a buttock side of the hip band portion and which are fixed on the thighs.

When putting the aforementioned medical corset on the body, the hip band portion is first wound around the hip region. The hip band portion, which is capable of entirely covering both the sacroiliac region and the hip joint region and is composed of an elastic material, keeps the hip region in a somewhat compressed condition. When the pair of femoral region holding means coupled to the hip band portion are fixed on the right and left thighs, then the attachment of the medical corset is completed. In this condition, in which the femoral region holding means are fixed on the thighs and are coupled on the buttock side, the entire corset is prevented from shifting upward even if bending and stretching are repeated, for example. The buttock side is the region extending from the buttocks to the back.

Accordingly, the femoral region holding means, when fixed, always keeps the position laced by the hip band portion, where the thighbone heads at the upper ends of the thighbones are pressed against the iliums. Hence, even if the coupling force between the iliums and the thighbones is low, the pressing force reinforces the coupling force to prevent the iliums and the thighbones from separating. This prevents the femoral nerves from being stimulated when the thighbones are moved.

The hip band portion wound around the hip region also covers and laces the sacroiliac region, which reinforces the coupling force between the iliums and the sacrum so that they can be fixed more firmly. This prevents the iliums and the sacrum from moving in an unusual direction with respect to each other, which prevents the sciatic nerves from being stimulated.

In another aspect of the present invention, when the femoral region holding means includes band bodies wound and fixed around the thighs, then just winding and fixing them around the thighs completes the attachment.

Furthermore, specific means for fixing both ends of the hip band portion and the band bodies wound around the hip region and the thighs may include means composed of a coupling member provided on one end of the hip band portion or one end of each band body and a coupled member provided on the other end to be detachably coupled to the coupling member. More specifically, the coupling member may be a male member of a plane fastener with the coupled member being a female member of the plane fastener.

When the band body is coupled in a certain area in the center part on its upper side to the hip band portion in its portion corresponding to the side of the buttock on its lower end, the boundary between them is flat without any difference in height, unlike one in which the band bodies and the hip band portion are coupled in an overlapped state.

Furthermore, when finger-pressure means for locally pressuring a region to be finger-pressured to cure a lame hip is provided in the hip band portion, its finger-pressure effect further lightens a lame hip.

As has been described above, according to the present invention, even if the sacroiliacs and the hip joints have a trouble, the sciatic nerves and the femoral nerves are prevented from being stimulated when the body is moved, which effectively prevents a lame hip due to the trouble in these joint regions.

According to another aspect of the present invention, only winding the hip band portion and the band bodies around the hip region and the femoral regions and fixing their both ends with male members and female members of plane fasteners completes attachment of the medical corset. The medical corset can thus be attached easily.

Moreover, the boundaries between the hip band portion and the band bodies are flat without any difference in level, which produces the effect that the medical corset well fits the body.

Furthermore, the finger-pressure means also functions to lighten the lame-hip, thus more effectively preventing a lame hip.

DESCRIPTION OF THE PREFERRED EMBODIMENTS

Figure 1:
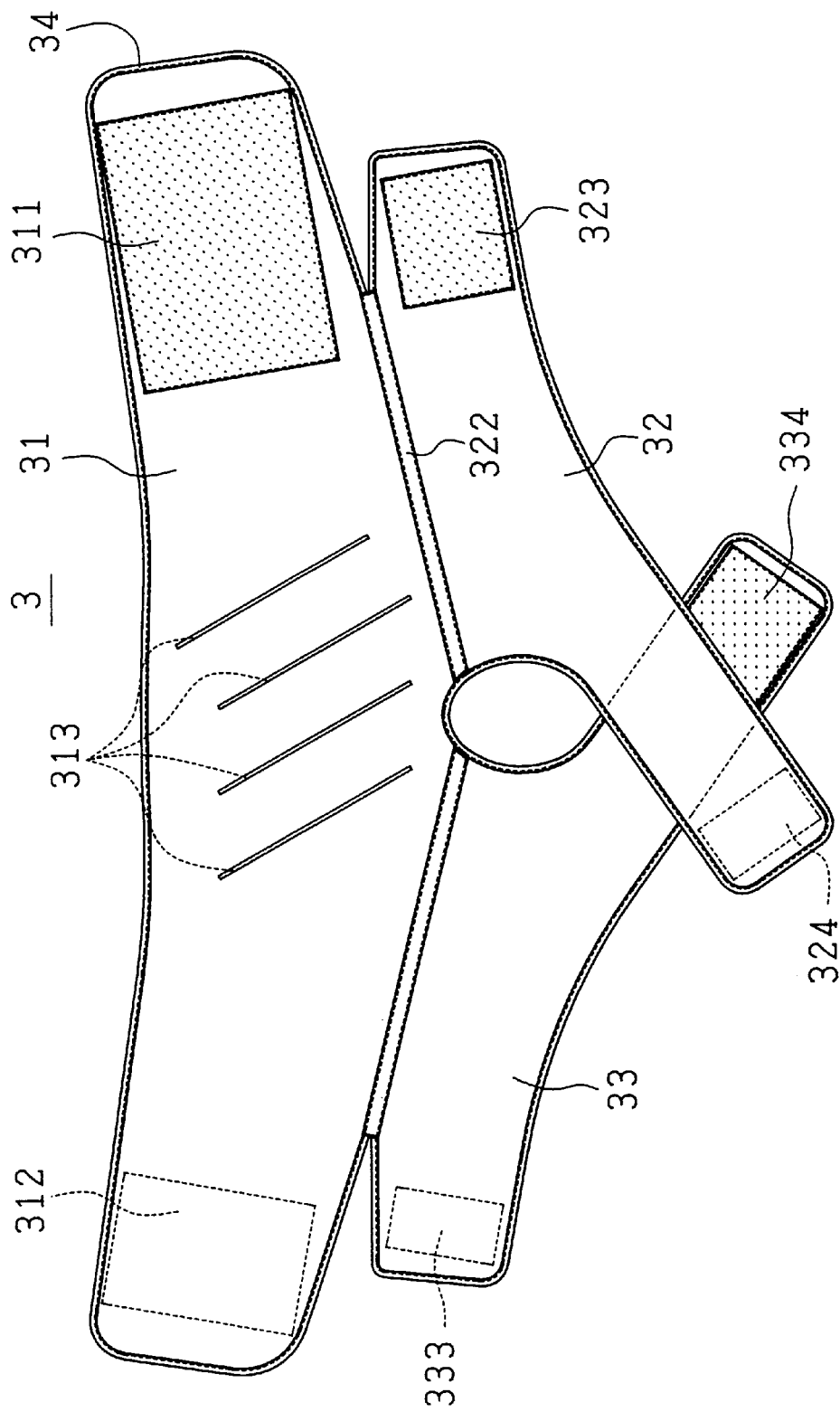
FIG. 1 is a plan of a medical corset according to an embodiment of the present invention.

A medical corset according to an embodiment of the present invention is formed of an elastic rubber sheet as a whole. A material composed of neoprene rubber with nylon jersey stuck thereon can be used, for example. As shown in FIG. 1, the corset includes a hip region lacing band 31 for surrounding the region from the back of the hip region to the abdominal region and femoral region winding bands 32, 33 coupled to its lower side in symmetrical positions. In this medical corset, in the entire surface including the hip region lacing band 31 and the femoral region winding bands 32, 33, the area wound around the hip region to entirely cover the sacroiliacs 13a, 13b and the hip joints 16, 16 when put on the body corresponds to the hip band portion mentioned above. In the femoral region winding bands 32, 33, the portion located below the hip band portion corresponds to the femoral region holding means mentioned above and the band bodies shown as its lower concept.

Figure 2:
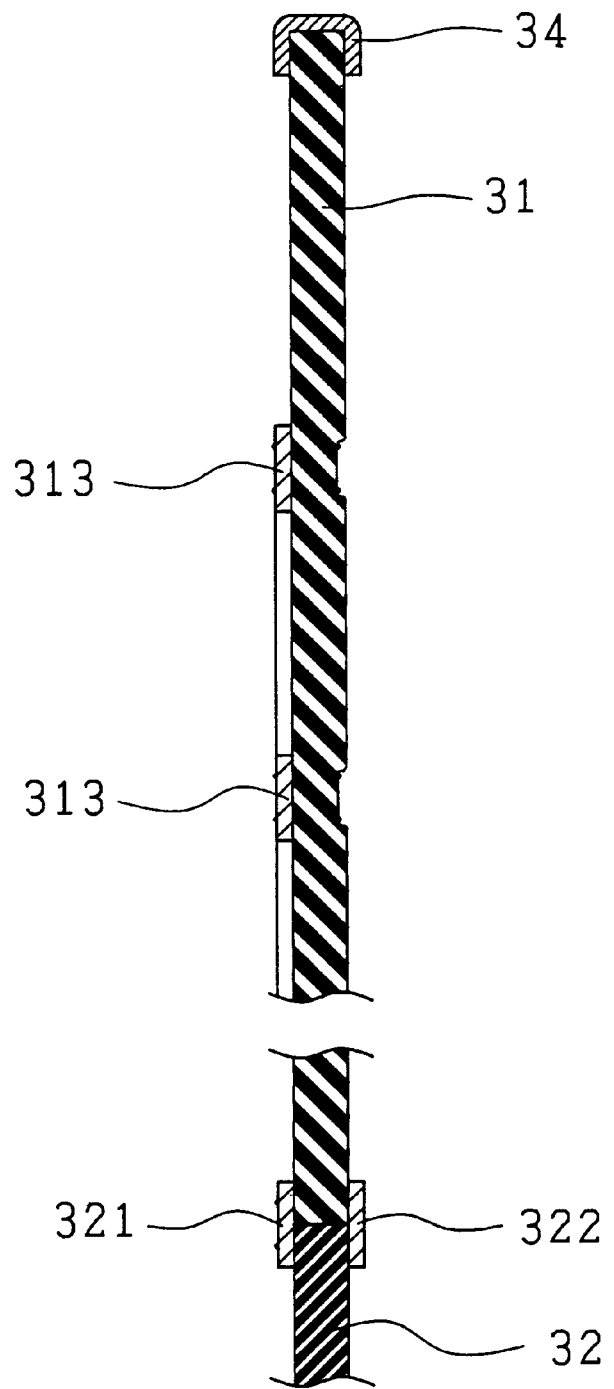
FIG. 2 is a sectional view of the hip portion of the medical corset 3 of FIG. 1.

A male member 311 and a female member 312 forming a plane fastener are sewn on the outer surface of one end of the hip region lacing band 31 and the inner surface of the other end. As shown in FIG. 2, a plurality of thick cloth tapes 313 are obliquely sewn on the inner surface of the hip region lacing band 31. The cloth tapes 313 locally press the skin on the back of the sacroiliacs 13a, 13b (the portion to which lame hip treatment can be effectively applied) to further lighten the lame hip. Accordingly, in this embodiment, the cloth tapes 313 correspond to finger-pressure treatment means.

The upper side of the femoral region winding band 32 is sewn to the lower side of the hip region lacing band 31 with the cloths 321, 322 applied on the front and back sides. A male member 323 and a female member 324 forming a plane fastener are respectively sewn on one end of the front side of the femoral region winding band 32 and its other end on the back side, similar to the hip region lacing band 31.

The femoral region winding band 33, which is shaped in a symmetrical form with respect to the femoral region winding band 32, also has a male member 333 and a female member 334 forming a plane fastener sewn on the end on the back side and on the end on the front side. The periphery of the medical corset 3 composed of the hip region lacing band 31 and the femoral region winding bands 32, 33 is covered with bias tape 34.

In this embodiment, the male members 311, 323 and 333 provided on the hip region lacing band 31 and the femoral region winding bands 32 and 33 correspond to the coupling members of this invention, and the female members 312, 324 and 334 correspond to the coupled members.

Figure 3:
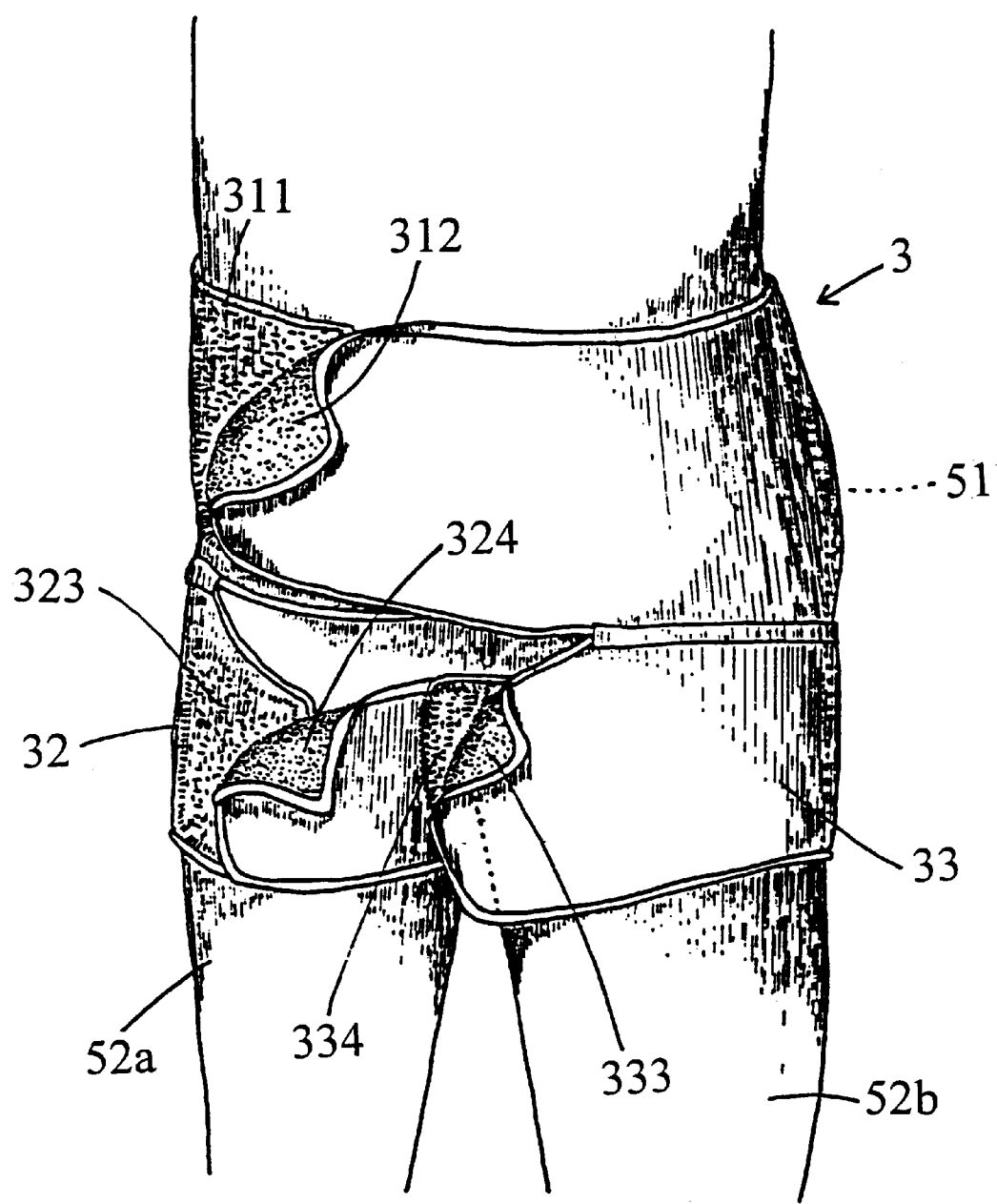
FIG. 3 is a perspective view of the medical corset 3 of FIG. 1 put on the body, seen from the front side of the body.
Figure 4:
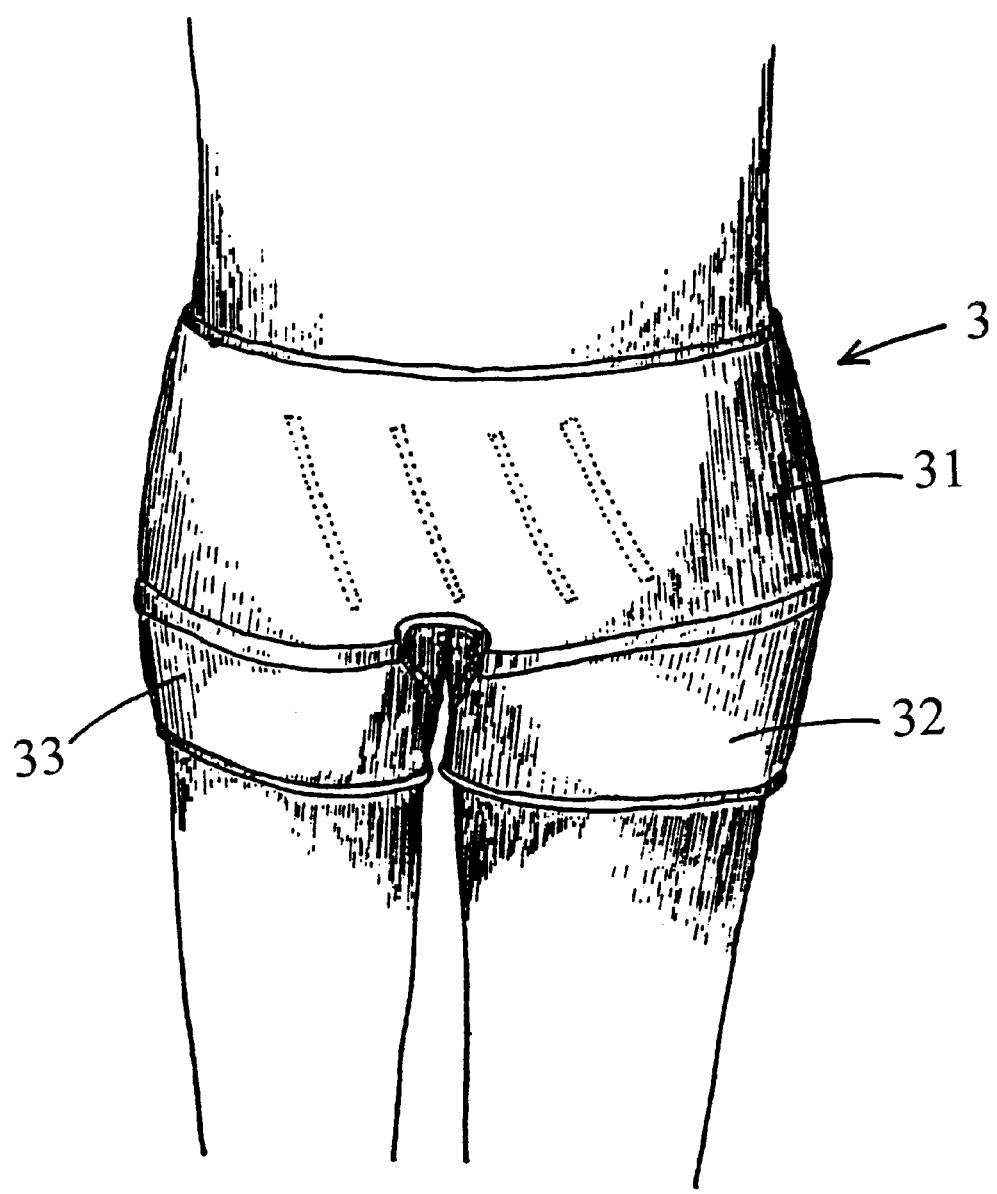
FIG. 4 is a diagram showing the medical corset 3 of FIG. 1 put on the body, seen from the back of the body.

The medical corset 3 of this embodiment is attached on a body as shown in FIG. 3 and FIG. 4.

The hip region lacing band 31 is wound from the buttocks to the abdomen 51 and its one end is laid on the other, which are coupled and fixed with the male member 311 and the female member 312 of the plane fastener. Next, the femoral region winding bands 32 and 33 are wound around the upper regions of the thighs 52a, 52b from the back and their respective two ends are coupled and fixed with the male and female members 323 and 324, 333 and 334 of the plane fasteners. Then the medical corset 3 has been put on the body as shown in the front view of FIG. 3 and the back view of FIG. 4. In this condition, the area including the upper parts of the thighs, the buttocks and the abdomen is entirely covered with the medical corset 3.

Figure 6:
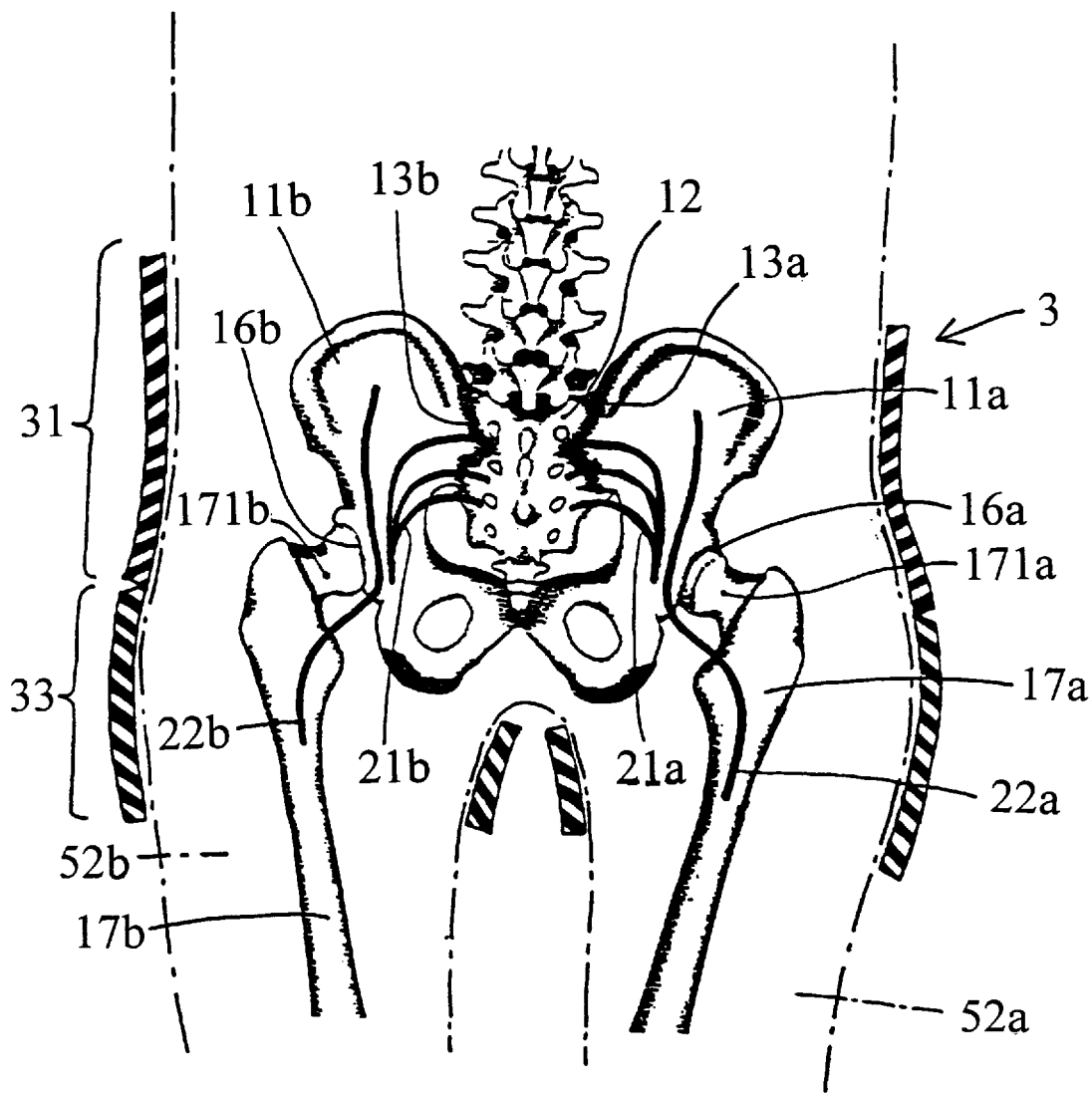
FIG. 6 is an explanation drawing seen from the back of the body for showing the positional relation between the medical corset 3 of FIG. 1 put on the body and the skeletal structure.
Figure 7:
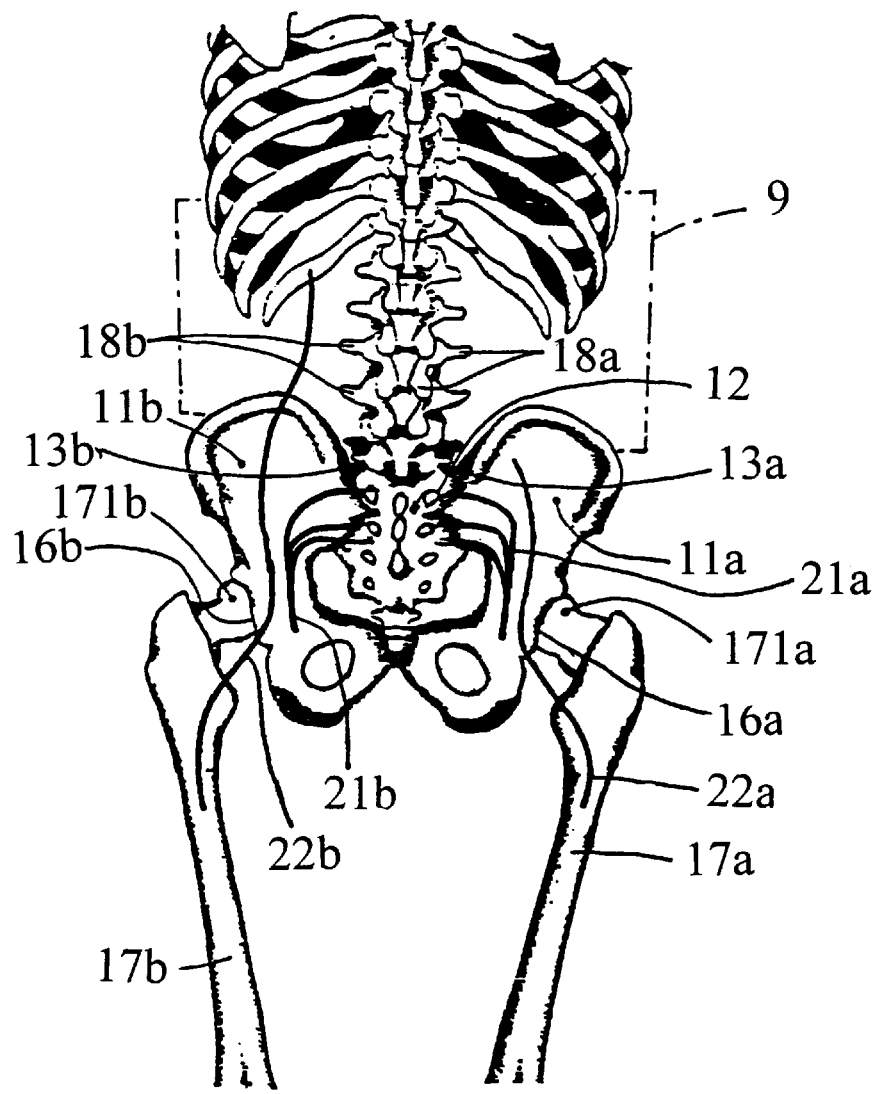
FIG. 7 is an explanation drawing seen from the back of the body for showing the positional relation between a conventional medical corset and the skeletal structure.

As shown in FIG. 6, when the medical corset 3 is put on the body, the hip region lacing band 31 formed of an elastic rubber sheet compresses the region of the sacroiliacs 13a, 13b to fix each of the sacrum 12, and each of the iliums 11a, 11b. Accordingly, each of the sacrum 12 and each of the iliums 11a, 11b are prevented from moving relatively to each other when the body moves, and then the sciatic nerves 21a, 21b running in their vicinities will not be stimulated.

Figure 5:
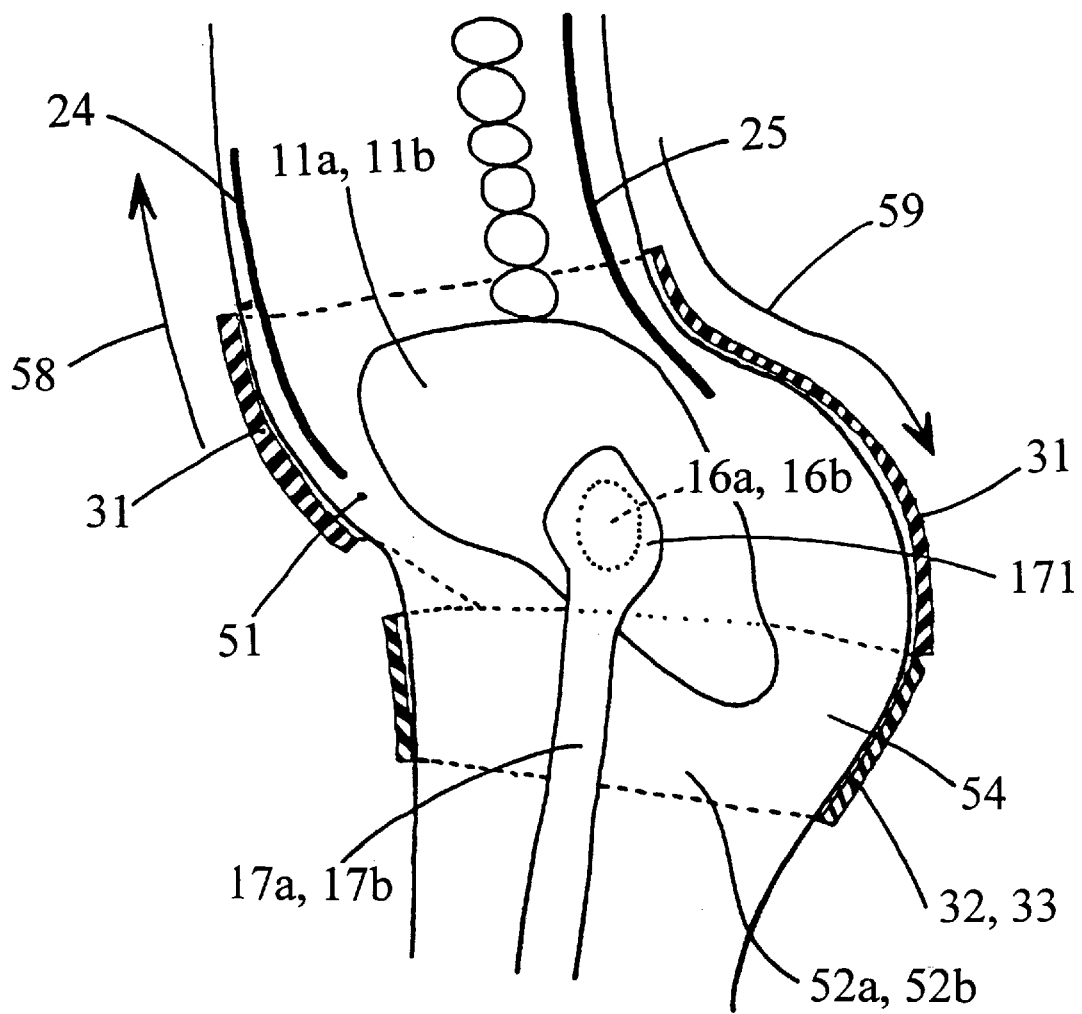
FIG. 5 is a longitudinal sectional view of the medical corset 3 of FIG. 1 put on the body.

Furthermore, since the region including the upper parts of the thighs, the buttocks and the abdomen is entirely covered by the hip region lacing band 31 and the like having the elasticity as shown in FIG. 5, the lower end of the hip region lacing band 31 is pulled down by the femoral region winding bands 32 and 33 when a sitting posture is assumed and therefore the buttocks 54 and the muscle erector spinae 25 above them are pulled downward as a whole, as shown by the arrow 59. The both ends of the hip region lacing band 31 and their vicinity compress the abdominal region 51 to lift up this region as shown by the arrow 58. Hence, when this medical corset 3 is attached, the abdominal muscle 24 is raised and the muscle erector spinae 25 on the back is pulled downward as shown by the arrows 58 and 59 so that the entire body is corrected to an upright posture. Thus the upright posture is ensured and therefore the weight acts in such a way that less load is applied to the hip region including the sacroiliac 13. This also works to ease a lame hip caused by a disease of the sacroiliac 13.

As shown in FIG. 5 and FIG. 6, the medical corset 3 laces the region of the hip joints 16a, 16b to press the heads 171a, 171b at the upper ends of the thighbones 17a, 17b against the respective iliums 11a, 11b. That is to say, if the connection between the thighbones 17a, 17b and the iliums 11a, 11b is unstable, it is stabilized. Accordingly, it prevents each of the thighbones 17a, 17b from moving in an unusual direction with respect to each of the iliums 11a, 11b, which prevents the femoral nerves 22a, 22b running near the hip joints 16a, 16b from being stimulated.

The male and female members 311, 312, 333, 334, 323, 324 of the plane fasteners are provided on ends of the hip region lacing band 31 and the femoral region winding bands 32, 33 in the embodiment above. However, they may be replaced by hooks composed of receiving and engaging parts which are detachably coupled, zippers composed of two rows of interlocking tabs attached to cloth tapes so that they can be joined and separated, buttons and button holes, strings which are tied with each other, or ring bodies to be individually fit around the individual legs, etc.

Although the medical corset according to the aforementioned embodiment compresses both the sacroiliacs and the hip joints, it may be constructed to compress one of the two.

While the invention has been described in detail, the foregoing description is in all aspects illustrative and not restrictive. It is understood that numerous other modifications and variations can be devised without departing from the scope of the invention.

I claim:

1. A medical corset, comprising:
   a hip band portion composed of an elastic material adapted to cover, both a sacroiliac region and a hip joint region of a user;
   finger-pressure means for applying a local pressure to a region to be finger-pressured to cure a lame hip provided on said hip band portion, said finger pressure means comprising a plurality of obliquely-arranged, thick cloth tapes positioned to press directly against a skin of the user; and
   a pair of femoral region holding means coupled to a rear side of said hip band portion and which are each fixable on a respective thigh of the user.

2. The medical corset according to claim 1, wherein each of said femoral region holding means includes a band body which is wound and fixable on the thigh.

3. The medical corset according to claim 2, wherein said band body has a coupling member provided on one ends and a coupled member provided on another end and which is detachably coupled to said coupling member.

4. The medical corset according to claim 3, wherein said coupling member includes a male member of a plane fastener, and said coupled member includes a female member of the plane fastener.

5. The medical corset according to claim 4, wherein a certain area of a central part on an upper side of said band body is coupled to a portion corresponding to a side of a buttock of the user, on a lower side of the hip band portion.

6. The medical corset according to claim 1, wherein when worn by the user, said corset substantially covers the buttocks, abdomen and upper thighs of the user.

7. A medical corset which can be freely attached to and detached from a body, comprising:
   compressing means, positionable on a body of a user, for compressing a sacroiliac region, said compressing means being comprised of an elastic material;
   holding means coupled to said compressing means and which is attachable on each respective thigh of the user to hold said compressing means to the body; and
   a plurality of raised regions on an inner surface of said compressing means, adapted to press directly against a skin of the user, for applying a localized pressure against a predetermined region of the user.

8. The medical corset according to claim 7, wherein said compressing means further compresses a hip joint region of the user.

9. A medical corset which can be freely attached to and detached from a body, comprising:
   compressing means for compressing a hip joint region of a user, said compressing means being comprised of an elastic material;
   holding means, coupled to said compressing means and which is attachable on each respective thigh of the user to hold said compressing means to the body; and
   a plurality of raised regions on an inner surface of said compressing means, adapted to press directly against a skin of the user, for applying a localized pressure against a predetermined region of the user.

10. The medical corset comprising:
    a hip band portion composed of an elastic material adapted to cover both a sacroiliac region and a hip joint region of a user, said hip band portion having two ends, a coupling member provided on one of the two ends, and a coupled member provided on the other of the two ends and which is detachably coupled to said coupling member;
    a pair of femoral region holding means coupled to a rear side of said hip band portion and which are each fixable on a respective thigh of the user, each of said femoral region holding means including a band body which is wound and fixable on the thigh, said band body having:
      two ends,
      a coupling member including a male member of a plane fastener provided on one of the two ends, and
      a coupled member including a female member of the plane fastener provided on the other of the two ends and which is detachably coupled to said band body coupling member, wherein a certain area of a central part on an upper side of said band body is coupled to a portion corresponding to a side of a buttock of the user, on a lower side of the hip band portion; and
    finger-pressure means for applying a local pressure to a region to be finger-pressured to cure a lame hip provided on said hip band portion, said finger pressure means comprising a plurality of obliquely-arranged, thick cloth tapes positioned to press directly against a skin of the user.

11. A medical corset, comprising:
    a hip band portion composed of an elastic material adapted to cover, both a sacroiliac region and a hip joint region of a user, wherein an inner surface of said hip band portion has a plurality of raised regions on a rear side thereof, for applying a localized pressure against the sacroiliac region of the user; and
    a pair of femoral region holding means coupled to the rear side of said hip band portion and which are each fixable on a respective thigh of the user.

* * * * *